(12) United States Patent
Boisseau et al.

(10) Patent No.: US 9,333,376 B2
(45) Date of Patent: May 10, 2016

(54) METHOD AND APPARATUS FOR CALIBRATING A CHARGED PARTICLE PENCIL BEAM USED FOR THERAPEUTIC PURPOSES

(71) Applicant: Pyramid Technical Consultants, Inc., Lexington, MA (US)

(72) Inventors: R. Paul Boisseau, Waltham, MA (US); John Gordon, Henfield (GB); William P. Nett, Waltham, MA (US)

(73) Assignee: Pyramid Technical Consultants Inc., Lexington, MA (US)

( * ) Notice: Subject to any disclaimer, the term of this patent is extended or adjusted under 35 U.S.C. 154(b) by 0 days.

(21) Appl. No.: 14/641,932

(22) Filed: Mar. 9, 2015

(65) Prior Publication Data
US 2015/0251021 A1    Sep. 10, 2015

Related U.S. Application Data

(60) Provisional application No. 61/949,551, filed on Mar. 7, 2014, provisional application No. 62/005,579, filed on May 30, 2014.

(51) Int. Cl.
| | |
|---|---|
| *A61B 6/00* | (2006.01) |
| *G01N 23/04* | (2006.01) |
| *A61N 5/10* | (2006.01) |
| *G01T 1/29* | (2006.01) |

(52) U.S. Cl.
CPC ............... *A61N 5/1075* (2013.01); *G01T 1/29* (2013.01); *A61N 2005/1087* (2013.01)

(58) Field of Classification Search
CPC ...... A61B 6/032; A61B 6/4085; A61B 6/027; A61B 6/4028; A61B 6/468; A61B 6/542; A61N 5/1049; A61N 5/1071; A61N 5/1075; G01N 23/046

USPC .......... 378/16, 19, 207, 95; 250/252.1, 354.1, 250/492.1, 505.1
See application file for complete search history.

(56) References Cited

U.S. PATENT DOCUMENTS

| | | | | |
|---|---|---|---|---|
| 4,868,843 | A * | 9/1989 | Nunan ................... | G21K 1/046 250/505.1 |
| 6,188,745 | B1 * | 2/2001 | Gordon .................. | A61B 6/032 378/15 |
| 7,371,007 | B2 * | 5/2008 | Nilsson ................. | A61B 6/542 378/207 |
| 8,611,490 | B2 * | 12/2013 | Zhang .................... | A61B 6/025 378/16 |
| 8,716,663 | B2 * | 5/2014 | Brusasco ................ | G01T 1/00 250/336.1 |
| 2002/0196893 | A1 * | 12/2002 | Gordon .................. | A61B 6/032 378/4 |
| 2008/0170663 | A1 * | 7/2008 | Urano ................... | A61N 5/1042 378/65 |
| 2011/0248188 | A1 * | 10/2011 | Brusasco ............. | A61N 5/1048 250/492.1 |
| 2011/0286646 | A1 * | 11/2011 | Chen .................... | G06T 11/006 382/131 |

(Continued)

*Primary Examiner* — David A Vanore
(74) *Attorney, Agent, or Firm* — Intrinsic Law Corp.; Ibrahim M. Hallaj

(57) ABSTRACT

A system for calibrating a charged particle pencil beam includes a first pixelated detector, a second pixelated detector, a beam stop, and a diagnostics system. The first and second pixelated detectors measure the pencil beam at positions proximal and/or distal to an isocenter plane. The beam stop is configured to detect an energy level of the pencil beam. The diagnostics system is configured to transmit a signal to request a generation of the charged particle pencil beam at different settings. The diagnostics system is also configured to update a calibration parameter for each setting based on the data received from the pixelated detectors and the beam stop.

23 Claims, 9 Drawing Sheets

(56) References Cited

U.S. PATENT DOCUMENTS

2015/0087885 A1* 3/2015 Boisseau ............ A61N 5/1043 600/1

2015/0251021 A1* 9/2015 Boisseau ............ A61N 5/1075 250/252.1

* cited by examiner

METHOD AND APPARATUS FOR CALIBRATING A CHARGED PARTICLE PENCIL BEAM USED FOR THERAPEUTIC PURPOSES

RELATED APPLICATIONS

This application is related and claims priority to U.S. Provisional Application No. 61/949,551 entitled, "A Method and Apparatus for Measuring the Quality of a Charged Particle Beam Used for Therapeutic Purposes," filed on Mar. 7, 2014, and U.S. Provisional Application No. 62/005,579 entitled "A Method and Apparatus for Measuring the Quality of a Charged Particle Beam Used for Therapeutic Purposes—II," filed on May 30, 2014, both of which are hereby incorporated herein by reference.

TECHNICAL FIELD

The present disclosure generally relates to therapeutic particle beams, and more specifically, to techniques and devices to design, test and benchmark the same in clinical and other applications.

BACKGROUND

Particle therapy, and specifically particle beam therapy using magnetic scanning or positioning of mono-energetic pencil beams is understood to offer advantages over other methods of treating localized cancer tumors. In pencil beam scanning, a narrow beam of ions such as protons or carbon nuclei, of known energy, intensity and transverse intensity distribution is directed to a notional treatment position called the isocenter. The beam spot is moved laterally across an isocenter plane to "paint" a layer or lateral distribution of therapeutic radiation dose according to a map derived from a treatment plan. This exercise is repeated at a number of beam kinetic energies, in the typical range 50 to 250 MeV for protons, so that the particles stop and deliver most of their dose at defined depths inside the patient, thus building up a volumetric distribution that is made to conform to the target tumor. In recent developments, the beam energy may be adjusted more frequently than every layer.

It is vital that the therapist can be sure that the system delivers therapeutic beams of radiation that are within acceptable tolerances of the beams assumed in the treatment plan. This requires knowledge of the position, shape, transverse intensity distribution, trajectory, divergence, delivered charge and kinetic energy of the particle beam. The same knowledge is required during initial commissioning of the system, when a large number of beam kinetic energy and delivery angles are characterized to build up a database of settings. This database can then be used to recall particular beams, and also provides input into the treatment planning system. This is a very time-consuming process that limits the rate of commissioning new particle therapy facilities. Existing beam quality measurement systems used in particle therapy are generally the same as, or derived from, prior equipment used to qualify X-ray radiotherapy equipment. While this may be a rational approach for the particle beam delivery system known as double scattering, it is inappropriate for pencil beam scanning.

X-ray radiotherapy beams are nominally uniform over the area being treated. Double-scattering particle therapy can be considered to be approximately the same in that the objective is to achieve uniformity over some area, and the beam energy is usually modulated quickly so that the deposition of dose in the patient is spread longitudinally to form the spread out Bragg peak (SOBP). The beam can therefore be considered as smoothly distributed in space and constant in time. Thus many prior art quality assurance methods involve the use of small ionization chambers immersed in a tank of water that simulates absorption in body tissues. Localized measurements can be reasonably assumed to represent the overall dose distribution. In pencil beam particle therapy this is not the case. The beam current, position and energy, and even shape can all be deliberately adjusted, or may alter. The beam quality measurement problem is local.

Prior art systems that have sought to address the particular needs of pencil beam scanning focus on only a part of the whole problem, or have shortcomings. For example, they may record the beam position but not its shape or trajectory. They may be fixed to the particle beamline so that they rotate with it, but this does not detect any errors in the rotation relative to the patient coordinate system. They may detect the beam current but not its energy. They may detect the beam shape in projection onto two orthogonal axes, but not its true two-dimensional profile. There is no prior art system that measures all the key parameters at the same time, as required for best quality assurance and speed.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the disclosure is directed to a system for calibrating a charged particle pencil beam. The system includes a first pixelated detector disposed at a proximal position to an isocenter plane. The first pixelated detector is configured to provide a first output representative of first data of the charged particle pencil beam. A second pixelated detector is disposed at a first position distal to the isocenter plane. The second pixelated detector is configured to provide a second output representative of second data of the charged particle pencil beam.

A beam stop is disposed at a second position distal to the second pixelated detector. The beam stop is configured to provide a third output representative of an energy of the charged particle pencil beam. The second pixelated detector is disposed between the isocenter plane and the beam stop;

A diagnostics system that includes a processor and a memory is configured (a) to transmit a signal to request a generation of the charged particle pencil beam at a plurality of settings; and (b) to update a calibration parameter for each setting based on at least one of the first output, the second output, and the third output.

Another aspect of the disclosure is directed to a method for calibrating a charged particle pencil beam system. The method includes transmitting a signal to request a generation of the charged particle pencil beam at a plurality of settings. The method also includes receiving, for each setting, first data representing a first transverse intensity distribution of the charged particle pencil beam at a first position, where the first position is proximal to an isocenter plane. The method also includes receiving, for each setting, second data representing a second transverse intensity distribution of the charged particle pencil beam at a second position, where the second position is distal to the isocenter plane. The method also includes receiving, for each setting, third data representing an energy measurement of the charged particle pencil beam. The method also includes updating a calibration parameter for each setting based on at least one of the first data, the second data, and the third data.

IN THE DRAWINGS

For a fuller understanding of the nature and advantages of the present invention, reference is be made to the following detailed description of preferred embodiments and in connection with the accompanying drawings, in which.

DETAILED DESCRIPTION

The present disclosure relates to systems and methods in the application of particle beam therapy. Specifically, the disclosure relates to systems and methods for calibrating a charged particle pencil beam system. The system includes a pair of two-dimensional sensing parallel plate ionization chambers located either side of the isocenter, a beam stop, and a diagnostic control system. The diagnostic control system can communicate with a beam control system to iteratively calibrate the charged particle pencil beam system over a range of settings.

An advantage to the system and methods disclosed herein includes the ability to measure and/or calibrate a charged particle pencil beam system in less time than existing system. In addition, more comprehensive measurements and/or calibrations can be performed using the disclosed system and methods.

The proceeding discussion is demonstrative of proton therapy systems; however, the present invention is not beyond the scope of other beams used for therapeutic purposes, such as, energetic photons, positive ions, neutrons or other hadrons or leptons.

An aspect of the invention combines a number of diagnostic devices, mechanisms and controls to provide all the necessary information for characterization and quality assurance of pencil beam scanning particle therapy systems.

One embodiment comprises a pair of two-dimensional sensing parallel plate ionization chambers located either side of the isocenter, plus a beam stop.

Figure 1:
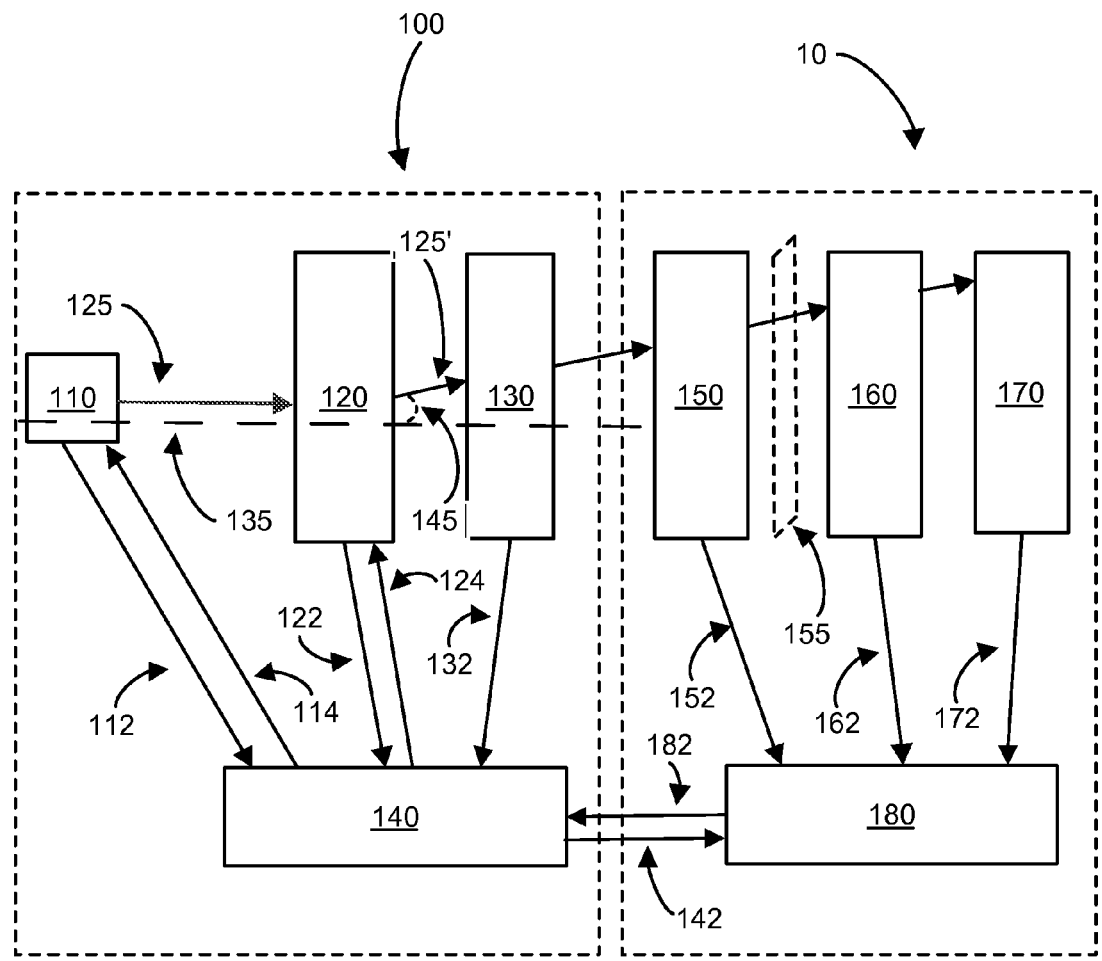
FIG. 1 illustrates a block diagram of a calibration system for a charged particle pencil beam delivery system.

FIG. 1 illustrates a plan view of a calibration system 10 for a charged particle pencil beam delivery system 100. The charged particle pencil beam delivery system 100 includes a charged particle pencil beam generator 110, a magnetic field generator 120, a detector 130, and a controller 140. The charged particle pencil beam generator 110 is configured to generate a charged particle pencil beam 125 (e.g., a proton beam) that travels towards the magnetic field generator 120 in a direction parallel to a reference axis 135. The magnetic field generator 120 includes magnetics and/or electromagnets that generate a magnetic field, which can cause deflect the charged particle pencil beam 125 laterally along a plane (e.g., an X plane) that is orthogonal to the reference axis 135. The deflected pencil beam 125' can travel at an angle 145 with respect to the reference axis 135, as illustrated in FIG. 1. The magnetic field generator 120 can adjust the lateral deflection and/or angle 145 to direct the deflected pencil beam 125' towards a target location in an isocenter plane 155, which represents a reference plane proximal to or within the patient. The isocenter plane 155 can be used to define and/or measure characteristics of the charged particle pencil beam 125 and/or the deflected charged particle pencil beam 125'.

The detector 130 can include one or more ionization chambers with strip or pixelated readouts as known in the art. In some embodiments, the detector 130 includes first and second strip detectors in which the first strip detector has strips of detector elements arranged in a first direction (e.g., a horizontal direction) and the second strip detector has strips of detector elements arranged in a second direction orthogonal to the first direction (e.g., a vertical direction). In some embodiments, the detector 130 can include two pairs of orthogonally-directed strip detectors (or two pixelated detectors) to provide, via output 132, a signal and/or data representing a first and second horizontal position and a first and second vertical position of the deflected charged particle pencil beam 125'. The output 132 can also include a signal and/or data representing the shape and/or transverse intensity distribution of the deflected pencil beam 125'.

The controller 140 is in communication with the charged particle pencil beam generator 110, the magnetic field generator 120, and the detector 130, as illustrated by the arrows in FIG. 1. The charged particle pencil beam generator 110 can send a signal 112 to the controller 140 that includes data that represents the actual output parameters of the charged particle pencil beam generator 110. Likewise, the magnetic field generator 120 can send a signal 122 to the controller 140 that includes data that represents the actual output parameters of the magnetic field generator 120. The controller 140 can provide a first feedback signal 114 to the charged particle pencil beam generator 110 based on the output 132 of the detector 130 and the actual output parameters provided in signal 112. In addition or in the alternative, the controller can provide a second feedback signal 124 to the magnetic field generator 130 based on the output 132 of the detector 130 and the actual output parameters provided in signal 122.

The calibration system 10 includes a first pixelated detector 150, a second pixelated detector 160, and a beam stop 170. The first pixelated detector 150 is disposed proximally to the isocenter plane 155. The second pixelated detector 160 is disposed distally to the isocenter plane 155. In some embodiments, the pixelated detectors 150, 160 are disposed at an equal distance from the isocenter plane 155. The pixelated detectors 150, 160 can be disposed at or near, for example between about 25 mm to about 75 mm on either side of, the isocenter plane 155 to detect the deflected pencil beam 125' at approximately the target location. In some embodiments, the first pixelated detector 150 is disposed about 50 mm proximally to the isocenter plane 155 and the second pixelated detector 160 is disposed about 50 mm distally to the isocenter plane 155. In general, the relative positions of the pixelated detectors 150, 160 are known for accurate measurement and calculation of the characteristics of the charged particle pencil beam 125 and/or the deflected charged particle pencil beam 125'.

The first and second pixelated detectors 150, 160 provide first and second output signals 152, 162, respectively, to a beam diagnostic system 180, as illustrated in FIG. 1. The output signals 152, 162 can be sent via a wired or a wireless connection, as known in the art. The output signals 152, 162 include data that represents shape, transverse intensity distribution, and location of the deflected pencil beam 125'. The location of the deflected pencil beam 125' at each pixelated detector 150, 160, which are at known positions, can be used by the beam diagnostic system 180 to determine the trajectory or divergence angle of the deflected pencil beam 125'. For example, combining the information from a pair of pixelated detectors 150, 160 that are separated by a known distance where the particles follow ballistic paths (or assumed to follow such paths) allows the beam trajectory and the divergence of the beam envelope to be calculated in orthogonal axes using simple trigonometry. In some embodiments, the first pixelated detector 150 is a low-resolution pixelated detector and the second pixelated detector 160 is a high-resolution pixelated detector having a plurality of sub-arrays. Alternatively, the first pixelated detector 150 can be a high-resolution pixelated detector having a plurality of sub-arrays and the second pixelated detector 160 can be a low-resolution pixelated detector. Such low- and high-resolution pixelated detectors are described in U.S. application Ser. No. 14/632,270, entitled "Multi-Resolution Detectors for Measuring and Controlling a Charged Particle Pencil Beam," assigned to the same assignee as this application, which is hereby incorporated herein by reference.

The beam stop 170 measures the energy of the deflected pencil beam 125'. The beam stop 170 can be a single block that can measure the total beam current. Alternatively, the beam stop 170 can be a multilayer structure that can measure the stopping range of the beam 125', and thus its kinetic energy. In addition, the total beam current of the beam 125' can be determined with the beam stop 170 having a multilayer structure by summing the current measured at each layer. The beam stop 170 provides a third output signal 172 to the beam diagnostic system 180. The third output signal 172 includes data that represents the total current and/or kinetic energy of the deflected pencil beam 125', as discussed above.

The beam diagnostic system 180 receives as inputs a controller output signal 142 from the controller 140 and the output signals 152, 162, and 172. The controller output signal 142 can include data that represents the requested output parameters of the charged particle pencil beam generator 110 and the magnetic field generator 120, the actual output parameters of the charged particle pencil beam generator 110 and the magnetic field generator 120, and the data from detector 130. The beam diagnostic system 10 can compare the data represented in the output signals 152, 162, and 172 from the data represented in the controller output signal 142 to calibrate the charged particle pencil beam delivery system 100. Calibration data can be sent by a signal 182 to the controller 140 to adjust the feedback signals 114, 124 accordingly (e.g., due to an offset between a requested and an actual parameter).

For example, the beam diagnostic system 180 can correlate the requested position of the deflected pencil beam 125' (requested by the controller 140), the actual output parameters of the magnetic field generator 130, the measured position of the deflected pencil beam 125' from the detector 130, and the measured position of the deflected pencil beam 125' at isocenter (as measured by and/or interpolated by the pixelated detectors 150, 160) to calibrate the position of the deflected pencil beam 125'. In another example, the beam diagnostic system 180 can correlate the requested energy of the deflected pencil beam 125' (requested by the controller 140), the actual output parameters of the charged particle pencil beam generator 110, the measured intensity distribution of the deflected pencil beam 125' from the detector 130, and the measured energy of the of the deflected pencil beam 125' at the isocenter 155 plane (as measured by beam stop 170) to calibrate the energy of the charged particle pencil beam 125 and deflected pencil beam 125'. In yet another example, the beam diagnostic system 180 can correlate the requested focus of the charged particle pencil beam 125 (requested by the controller 140), the actual output parameters of the charged particle pencil beam generator 110, the measured shape of the deflected pencil beam 125' from the detector 130, and the measured shape of the deflected pencil beam 125' at isocenter (as measured by pixelated detectors 150, 160) to calibrate the focus of the charged particle pencil beam 125 and deflected pencil beam 125'.

In some embodiments, the beam diagnostic system 180 communicates with the controller 140 to automatically calibrate one or more parameters of the charged particle pencil beam delivery system 100. For example, the beam diagnostic system 180 can request, via the controller 140, that the charged particle pencil beam generator 110 generate the charged particle pencil beam 125 at a range of energies. The request can be made iteratively to calibrate the energy output of the particle pencil beam generator 110. Likewise, the beam diagnostic system 180 can request, via the controller 140, that the magnetic field generator 130 output a magnetic field of various strengths to deflect the charged particle beam 125 to various locations on the isocenter plane 155. The request can be made iteratively to calibrate the strength of the magnetic field output by the magnetic field generator 130. A similar iterative process can occur to calibrate the focus and gantry angle. In some embodiments, two or more parameters can be adjusted simultaneously for calibration, for example using statistical methods known in the art.

In some embodiments, the beam diagnostic system 180 interlocks some or all treatment conditions if one or more measurements, calibration, and/or treatment parameters are out of tolerance. The beam diagnostic system 180 can display the status or progress of the calibration on a video display having a user interface. In addition or in the alternative, the beam diagnostic system 180 can sends its data records to a database which can be linked to a more general data archive and distribution system.

Figure 2:
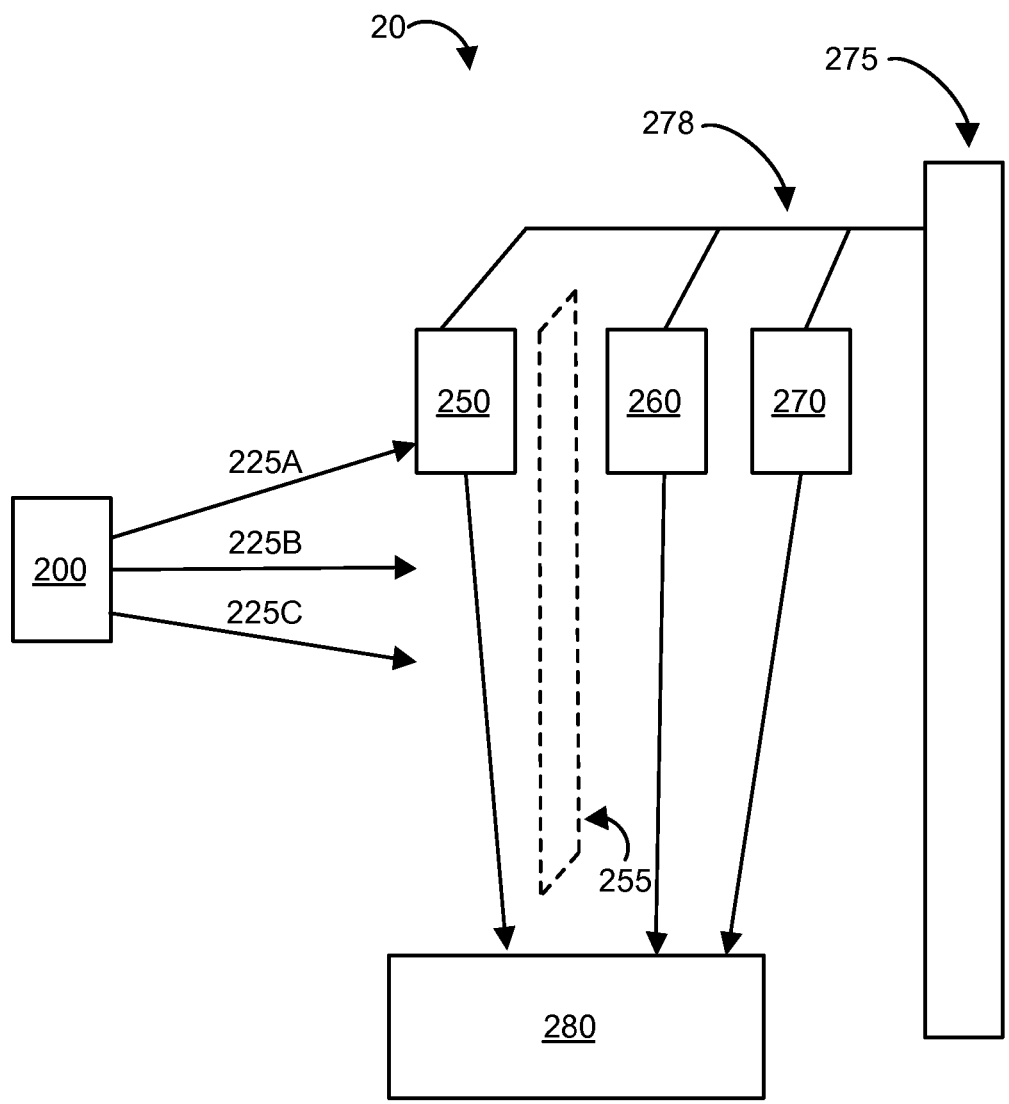
FIG. 2 illustrates a block diagram of a calibration system connected to a motion system.

FIG. 2 illustrates a plan view of a calibration system 20 connected to a motion system 275. The calibration system 20 includes first and second pixelated detectors 250, 260, a beam stop 270, and a beam diagnostic system 280, as described above. The detectors 250, 260 and beam stop 270 are connected to a motion system 275 by a support structure 278. The motion system 275 moves the calibration system 20 in a first direction parallel to the isocenter plane 255. As illustrated, the motion system 275 moves the calibration system 20 in a vertical and/or horizontal direction to align with charged particle pencil beams 225A, 225B, and 225C, which are generated at various angles by charged particle pencil beam delivery system 200. It is noted that only three calibrate charged particle pencil beams 225A, 225B, and 225C (and respective angles) are illustrated in FIG. 2 for illustrative purposes; additional beam angles can be employed. The motion system 275 can be a robotic arm, a mechanized belt, a lift assembly, or similar device known in the art.

A technical advantage to providing the motion system 275 is that the components of calibration system 20 can be smaller in size since they can be moved by the motion system 275 to detect a wide range of angles of charged particle pencil beams 225A, 225B, and 225C. Since the components are smaller, they can be less expensive and less complex than larger components that can cover a greater portion of the isocenter plane 255.

Figure 3:
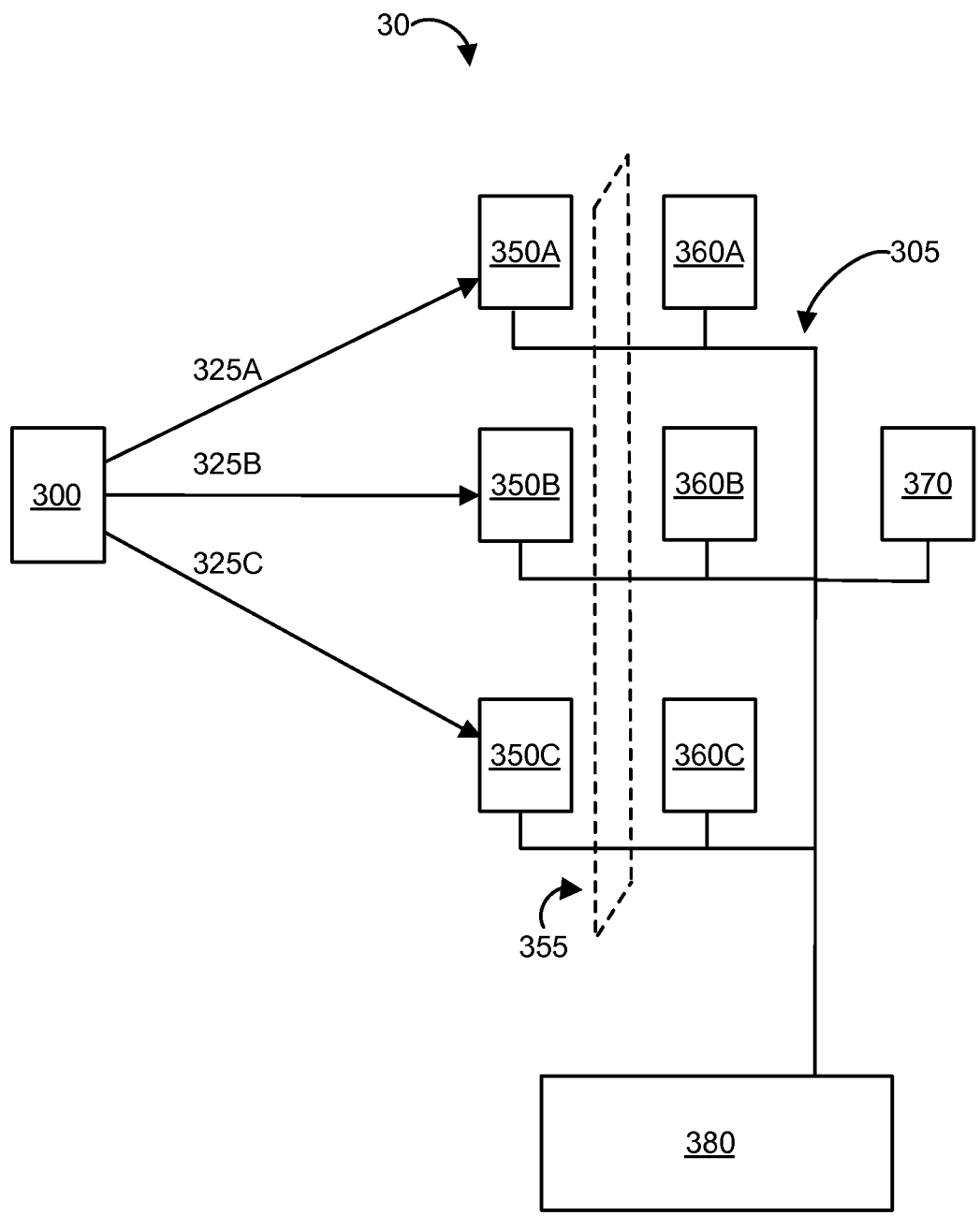
FIG. 3 illustrates a block diagram of a calibration system.

FIG. 3 illustrates a plan view of a calibration system 30. The calibration system 30 includes a first pair of pixelated detectors 350A, 360A, a second pair of pixelated detectors 350B, 360B, a third pair of pixelated detectors 350C, 360C a beam stop 370, and a beam diagnostic system 380. Multiple pairs of pixelated detectors 350N, 360N can be provided instead of, or in addition to, the motion system 275 described above. Each pair of pixelated detectors 350N, 360N can be identical or different. In some embodiments, a higher resolution may be preferred at a certain location and a correspondingly pair of high-resolution pixelated detectors 350N, 360N can be disposed at that location. In some embodiments, there can be up to 17 pairs of pixelated detectors 350N, 360N for adequate coverage of the isocenter plane 355. To avoid the need for an excessive number of readout channels, which would be required for each pixelated detector 350N and 360N, the corresponding pixels of each detector 350N, 360N can optionally be connected together in a multiplex arrangement 305. In any case, the pixelated detectors 350N, 360N are in communication with the beam diagnostic system 380, as described above.

As illustrated in FIG. 3, only one beam stop 370 is provided. This is because the energy of the pencil beam 325N is generally independent of the deflection angle and, thus, multiple beam stops are not generally required. However, additional beam stops 370n can be provided as necessary.

Figure 4:
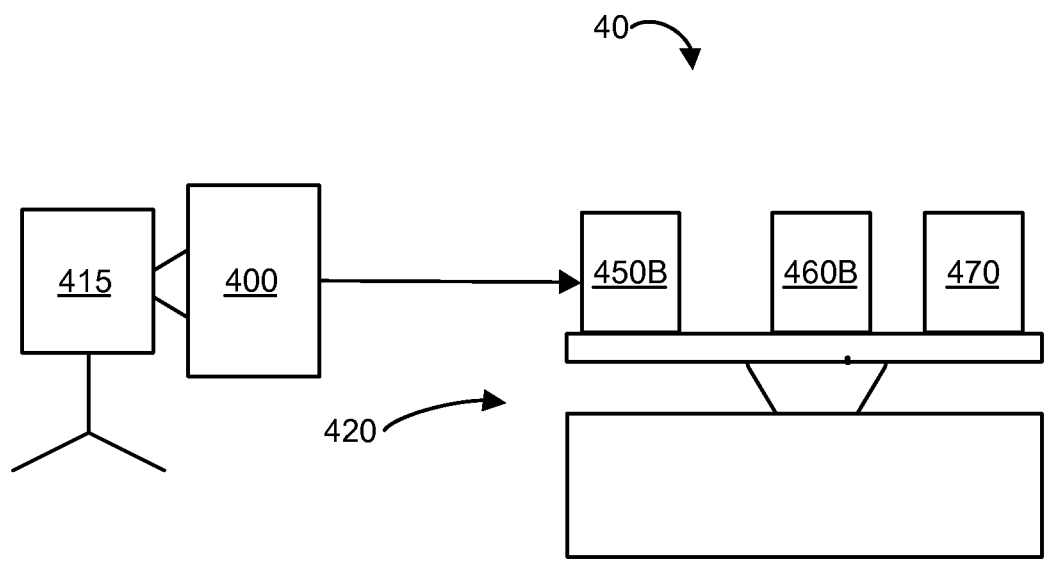
FIG. 4 illustrates a rotation mechanism to track the positions of a beamline gantry rotation mechanism.
Figure 5:
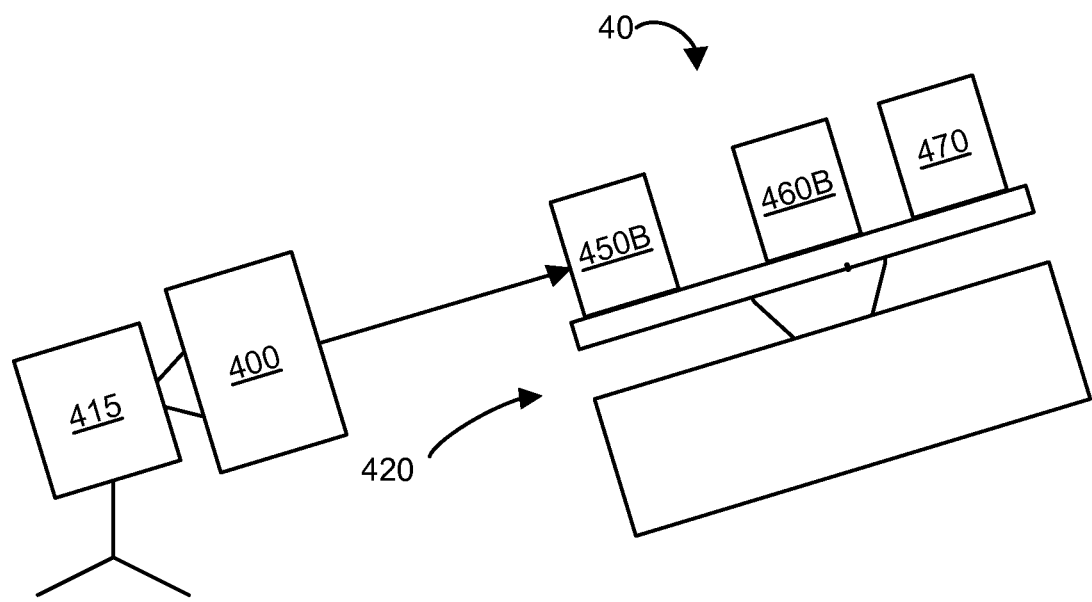
FIG. 5 illustrates a rotation mechanism to track the positions of a beamline gantry rotation mechanism.

Many particle therapy treatment rooms include a beamline gantry system that allows the beam to be directed towards the patient from a range of angles. There can be deviations in the beam direction as a function of gantry angle due to mechanical imperfections and the like. Further, the center defined by the average of all gantry angles will not exactly match the isocenter as defined by other equipment like the patient positioning and patient imaging systems. It may be desirable to quantify these errors so that they can be corrected for in beam delivery. The whole sensor array of the diagnostic system is therefore able to be precisely aligned to a particular coordinate system, generally the coordinate system defined by imaging and positioning a patient, and to rotate about this center on a precision gimbal so that it is always normal to the nominal undeflected particle beam direction. FIG. 4 illustrates the use of a rotation mechanism 420, referenced to the treatment coordinate system, to track the positions of a beamline gantry rotation mechanism 415. The beam gantry 415 can rotate the beamline components 100 and thus the beam itself to various angles, as illustrated in FIG. 5. The rotation mechanism 420 can rotate the beam diagnostics components, understood to include any embodiment described herein including a lateral translation motion system (e.g., as illustrated in FIG. 2) or multiple instances of the pixelated ionization chambers (e.g., as illustrated in FIG. 3) about a point that is carefully matched to the treatment coordinate system. The rotation mechanism 420 can provide an output that represents the angle of rotation, which can be used by the beam diagnostic system to calibrate the beam gantry 415.

Figure 6:
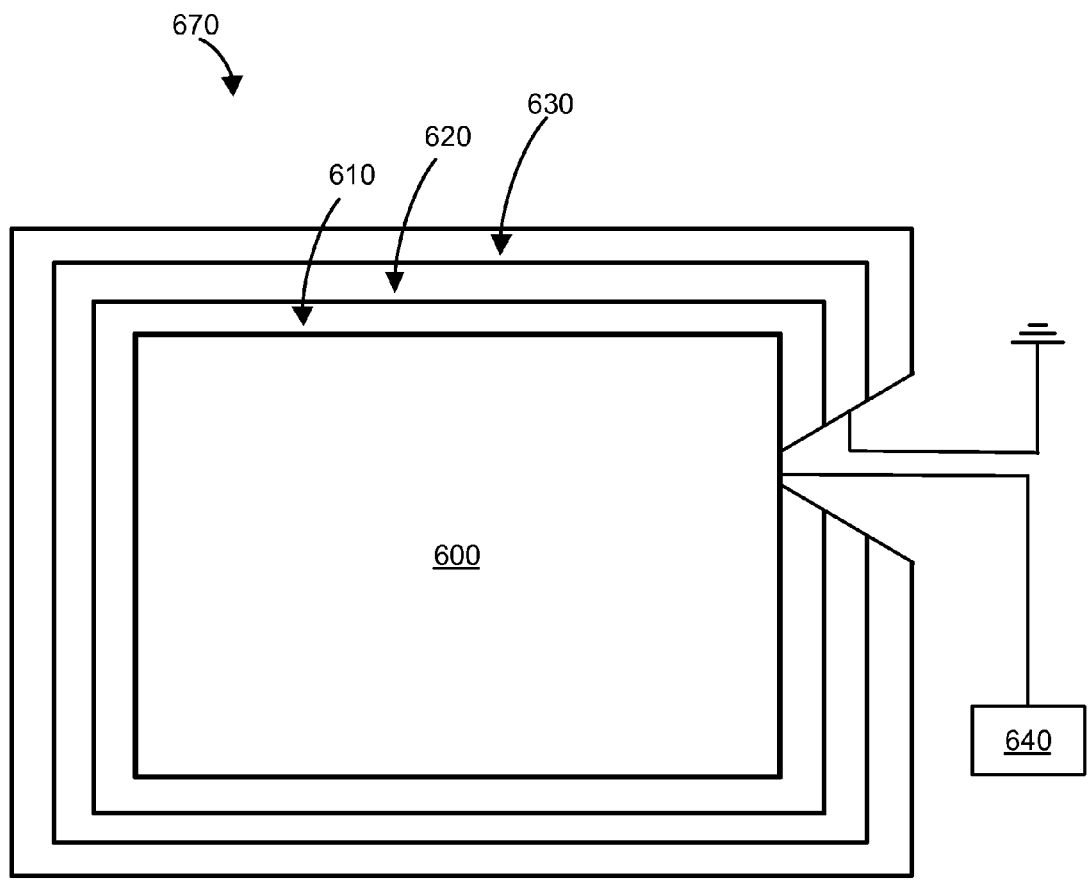
FIG. 6 illustrates a monolithic beam stop.

FIG. 6 illustrates a monolithic beam stop 670, which is also known as a monolithic Faraday collector. The beam stop 670 includes a metal block 600 coated by a first material layer 610, a second material layer 620, and a third material layer 630. A current measurement unit 640 is connected to the block 600 to provide an accurate and/or sensitive current measurement. The metal block 600 can be formed of copper, tungsten, and/or a similar material. In addition, the metal block 600 can have a thickness sufficient to stop the highest-energy particles of interest inside the block 600. The thickness of the metal block 600 is measured along the direction of travel of the charged particle pencil beam, from a first side of the metal block 600 that faces the charged particle pencil beam to a an opposing side of the metal block. For example, if the metal block 600 is formed of copper, the thickness can be at least 6.3 cm to stop a charged particle pencil beam having 250 MeV protons. Likewise, if the metal block 600 is formed of tungsten, the thickness can be at least 3.8 cm to stop a charged particle pencil beam having 250 MeV protons. The metal block 600 can have a width and/or diameter (measured along a plane that is perpendicular to the thickness of the block 600) that is at least sufficient to intercept the diameter of the charged particle pencil beam. In some embodiments, the metal block 600 can have a width and/or diameter that is greater than the diameter of the charged particle pencil beam, for example to account for lateral scattering of the pencil beam inside the block 600.

The first material layer 610 can conformally coat the metal block 600. The first material layer 610 can be a polyimide, such as KAPTON® (E. I. du Pont de Nemours and Company) or JARO 650 Series Polyimide (Jaro Corp.), or similar dielectric material with good radiation hardness, such as the ability to retain a property of interest (e.g., high resistivity) after exposure to radiation. For example, a polyimide can retain a high resitivity after exposure to radiation of $1\times10^6$ Gy and/or $1\times10^7$ Gy. In some embodiments, the first material layer 610 can be formed of a ceramic material with good radiation hardness. In some embodiments, the first material layer 610 can be between 25 to 150 microns thick. The first material layer 610 can be deposited on the metal block using processes known in the semiconductor arts, such as spin-on coating and/or a vacuum-based deposition with thermal curing.

The second material layer 620 can conformally coat the first material layer 610. The second material layer 620 can be a grounded screen layer such as a conductive epoxy (e.g., a silver epoxy). The second material layer 620 can be deposited on the metal block using processes known in the semiconductor arts, such as spin-on coating and/or a vacuum-based deposition with thermal curing.

The third material layer 630 can conformally coat the second material layer 620. The third material layer 630 can be a protective coating as a clear epoxy. The third material 630 can be deposited on the metal block using [processes known in the semiconductor arts, such as spin-on coating and/or a vacuum-based deposition with thermal curing.

Figure 7:
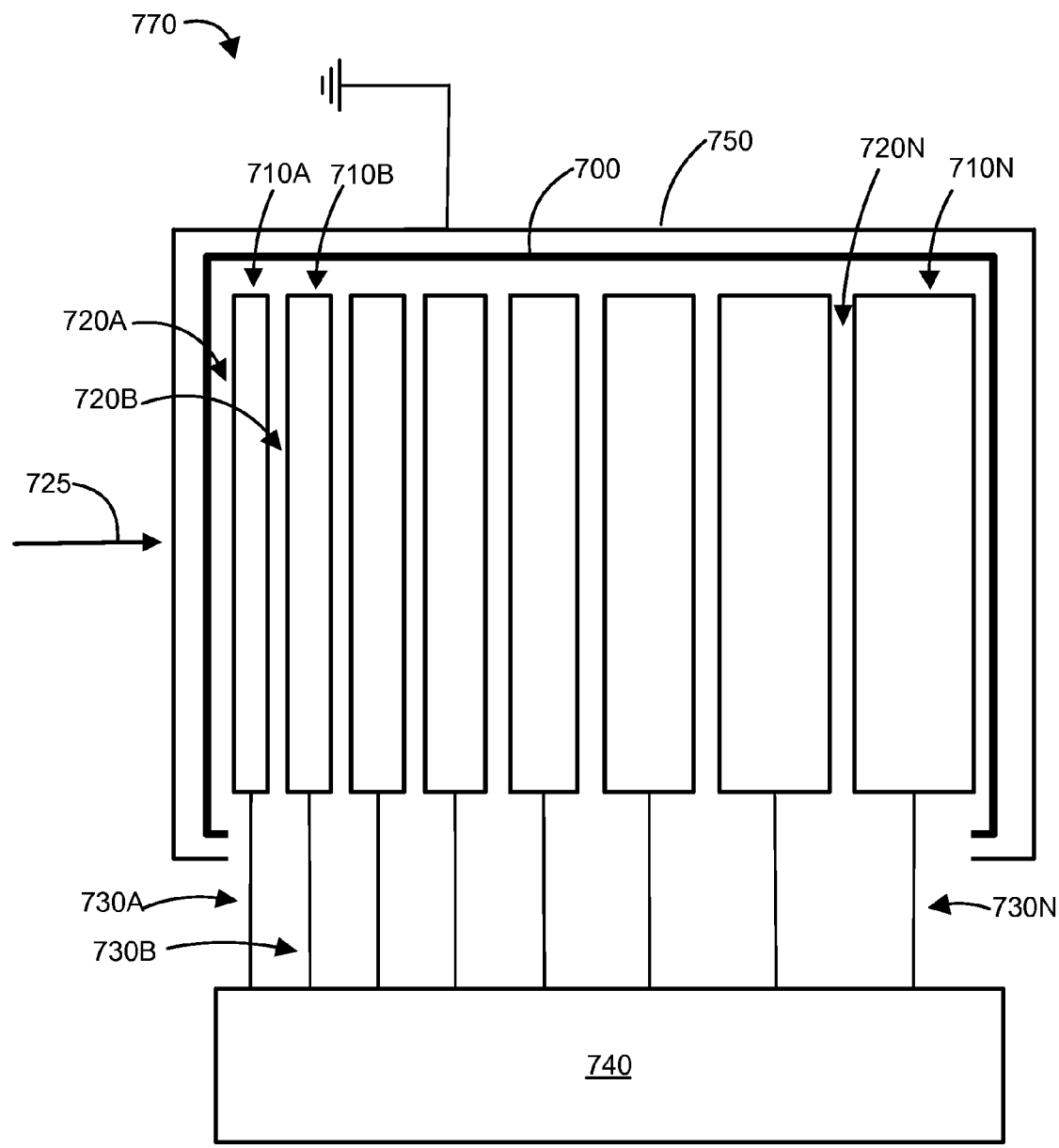
FIG. 7 illustrates a multilayer beam stop.

FIG. 7 illustrates a multilayer beam stop 770, which is also known as a multilayer Faraday collector. The beam stop 770 includes a metal block 700 formed of multiple metal layers 710A, 710B . . . 710N (generally 710n) with an insulation layer 720A, 720B . . . 720N (generally 720n) adjacent each metal layer 710N. The metal layers 710n are similar in height and can have a varying width along a direction of travel of a charged particle pencil beam 725. In some embodiments, the metal layers 710n each have an identical thickness. The width of metal layers 710n can increase from narrower to wider as the beam 725 passes through the metal block 700. In other words, metal layer 710A can have the narrowest width and metal layer 710N has the widest width. In some embodiments, the width of the metal layer 710 is the same or substantially the same across the metal block 700. In some embodiments, the beam stop 770 can include between about 50 to about 200 metal layers 710n. The metal block 700 and metal layers 710n can be made out of about 0.5 mm to about 5 mm thick or any width there between including 1 mm, 2 mm, 3 mm, or 4 mm (or a fraction thereof). In some embodiments, the metal block 700 has at least 128 metal layers 710n that are each about 0.5 mm thick. Each metal layer 710N is in electrical communication with a current measurement unit 740, for example through a respective wire 730A, 730B . . . 730N. It is noted that the bottom portion of the metal block 700 and a grounded shell 750 is not depicted in FIG. 7 to more clearly illustrate wires 730N. The width of the metal layers 710N can vary, as illustrated in FIG. 7 and described above, to reduce the number of channels while maintaining the desired resolution of the beam stop 770. The size of the metal block 700 and/or the width of the metal layers 710N can be selected for stopping the highest kinetic energy beam particles of interest.

The insulation layers 720n can be made out of a polyimide film, such as KAPTON® (E. I. du Pont de Nemours and Company) or JARO 650 Series Polyimide (Jaro Corp.) and can have a width of between about 10 microns to about 30 microns. The insulation layers 720n can have a good radiation hardness, for example as described above. The grounded shell 750 surrounds the metal block 700 to electrically isolate the metal block 700. The grounded shell 750 can be made out of steel, aluminum, copper, and/or a similar conductive material and can have a width of about 1 mm to about 5 mm or about 2 mm to about 4 mm or about 3 mm. In some embodiments, the grounded shell 750 can provide mechanical rigidity and/or support to the multilayer beam stop 770.

In operation, the beam 725 passes into the metal block 700. Depending on its kinetic energy, the beam 725 will pass to further into the block 700 across a greater number of metal layers 710N. A beam 725' that has a relatively low kinetic energy may only pass through two metal layers 710n (e.g., 710A and 710B) while a beam 725'' that has a relatively high kinetic energy may pass through six metal layers 710N. In some embodiments, a relatively low kinetic energy beam 725' can pass through between about 20 to 60 metal layers 710n while a relatively high-energy beam 725'' can pass through 100 to 120 metal layers 710n. The metal layer 710n at which the beam 725 stops can emit a current that can be detected by the current measurement unit 740. In some embodiments, multiple metal layers 710n emit a current, which can be interpolated for enhanced measurement resolution. For example, the width of the metal layers 710n can be selected so that at least two or three layers 710n produce a signal (e.g., a current), thus allowing interpolation of the signals to enhance measurement resolution. In some embodiments, the thicknesses of the metal layers 710n are carefully chosen following computer modeling and experiment, so that the charge due to all secondary electrons that are not both formed and stopped in the metal block 700 is reduced to a minimum.

The current measurement unit 740 can detect the peak of the current output from the metal layers 710n by interpolation of the data. The peak of the current output can correspond to the average kinetic energy of the beam 725. The total beam current can be determined by summing all the channels that contribute to the range curve. The total beam current can be degraded by a few percent due to a loss or gain of secondary electrons in the beam stop 770. Such a loss or gain can be mitigated through the design of the beam stop 770, as recognized by those skilled in the art. The readings can also provide a measurement of the energy spread of the beam 725.

The components of the beam diagnostics system may be integrated by computer controls. A communications channel from the beam diagnostics system computer to the control system of the particle therapy machine allows the process of making the measurements to be fully automated. The diagnostics system can request sequentially changes of beam kinetic energy, beam intensity, beam focus settings, gantry rotation angle and beam lateral deflection. In this way a large parameter space can be measured without need of operator intervention.

Figure 8:
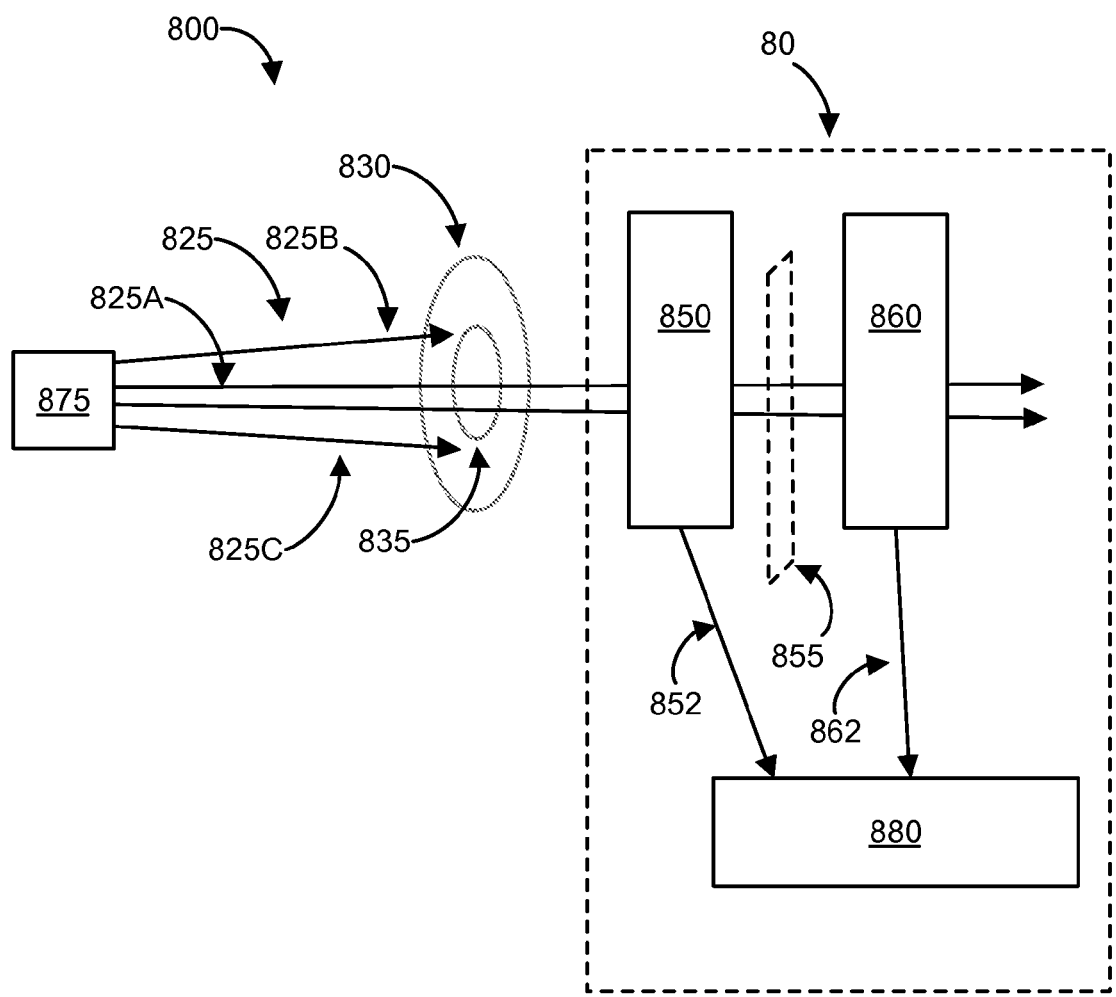
FIG. 8 illustrates a system for aligning beam diagnostics with an x-ray source.

FIG. 8 illustrates a system 800 for aligning beam diagnostics 80 with an x-ray source 875. The x-ray source 875 generates x-ray pulses 825 towards a collimating metal disk 830. Collimated x-ray pulses 825A can pass through an aperture 835 in the collimating metal disk 830. Diverging x-ray pulses 825B, 825C are stopped by collimating metal disk 830 and do not pass through the aperture 835. The collimated x-ray pulses 825A also pass into the beam diagnostics 80 including a first pixelated detector 850 and a second pixelated detector 860. The first and second pixelated detectors 850, 860 can be the same as the pixelated detectors described above.

In practice, the x-ray source 875 can be a component of a patient imaging system for aligning a position of a patient with a charged particle pencil beam. The aperture 835 is configured to be in mechanical alignment with the x-ray source 875. Thus, the beam diagnostics 80 can determine the position(s) (e.g., centroid(s)) and trajectory of the collimated x-ray pulses 825, which can be used to align the beam diagnostics 80 with the x-ray source 875. This allows the charged particle pencil beam trajectories to be expressed in the coordinate system of the x-ray system, which can enhance alignment of the beam diagnostics 80 and x-ray source 875.

An aspect of the present system is to verify that the coordinate system assumed by the treatment plan is accurately aligned with the coordinate system of the treatment hardware. The charged particle pencil beam system can include internal fiducials to allow optical and mechanical alignment with the facility hardware. An x-ray imaging system is typically used to align the patient before treatment. The disclosed system includes the capability to align directly to the diagnostic x-ray system. An X-ray-opaque aperture is inserted in the imaging system, and the ion-chamber pair is used to determine the precise position and trajectory of the central ray of the x-ray system.

Figure 9:
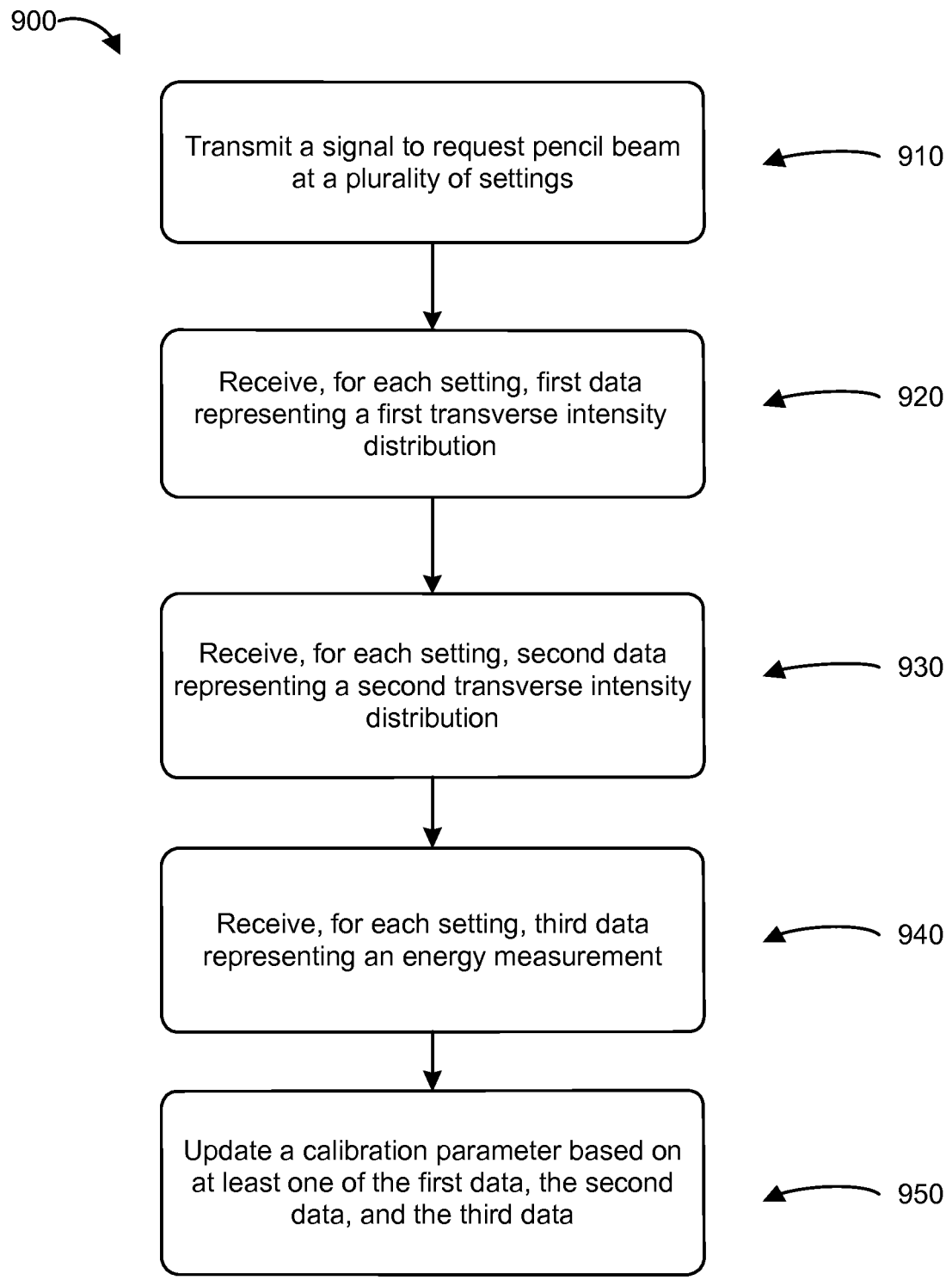
FIG. 9 is a flow chart of an exemplary method of calibrating a charged particle pencil beam system.

FIG. 9 is a flow chart 900 that illustrates an exemplary method of calibrating a charged particle pencil beam system. In 910, a signal is transmitted to request a generation of a charged particle pencil beam at a first setting. The signal can be sent by a beam controller or a diagnostic system controller. The setting can include an energy level (e.g., total current or kinetic energy), a focus (e.g., beam width), a magnetic field strength, a physical position of the charged particle pencil beam generator (e.g., gantry angle), or the like.

In 920, first data representing a first transverse intensity distribution of the charged particle pencil beam at a first position is received for each setting. The first position can be proximal to or at an isocenter plane. The first data can be generated by a pixelated detector, a pair of vertical and horizontal strip detectors, or similar device. The first data can also include a shape and/or a physical location of the charged particle pencil beam. The diagnostic system controller and/or the beam controller can receive the first data.

In 930, second data representing a second transverse intensity distribution of the charged particle pencil beam at a second position is received for each setting. The second position can be distal to or at an isocenter plane. The second data can be generated by a pixelated detector, a pair of vertical and horizontal strip detectors, or similar device. The second data can also include a shape and/or a physical location of the charged particle pencil beam. The diagnostic system controller and/or the beam controller can receive the second data.

In 940, third data representing an energy measurement of the charged particle pencil beam is received for each setting. The energy measurement can be a kinetic energy and/or a total current of the charged particle pencil beam. The third data can be generated by a beam stop, such as a monolithic or multilayer beam stop. The diagnostic system controller and/or the beam controller can receive the third data.

In 950, a calibration parameter is updated for each setting based on at least one of the first data, the second data, and the third data. The calibration parameter can be a multiplier, an offset, or similar correction for a given setting. For example, a setting of a 10 degree deflection angle (or a magnetic field strength corresponding to such a deflection angle) can updated with a calibration parameter of a +1 degree offset due to a measured value of a 9 degree deflection angle.

In some embodiments, the setting includes a focus, a magnetic field strength, a deflection angle, a gantry angle, and an energy level of the charged particle pencil beam. In some embodiments, the method includes determining a first centroid position of the first transverse intensity distribution and a second centroid position of the second transverse intensity distribution. In some embodiments, updating the calibration parameter includes comparing a model beam characteristic (e.g., a desired deflection angle of 10 degrees and/or a model energy setting) with a measured beam characteristic (e.g., a measured deflection angle of 9 degrees and/or a measured kinetic energy).

The present invention should not be considered limited to the particular embodiments described above, but rather should be understood to cover all aspects of the invention as fairly set out in the attached claims. Various modifications, equivalent processes, as well as numerous structures to which the present invention may be applicable, will be readily apparent to those skilled in the art to which the present invention is directed upon review of the present disclosure.

What is claimed is:

1. A system for calibrating a charged particle pencil beam, the system comprising:
    a first pixelated detector disposed at a proximal position to an isocenter plane, the first pixelated detector configured to provide a first output representative of first data of the charged particle pencil beam;
    a second pixelated detector disposed at a first position distal to the isocenter plane, the second pixelated detector configured to provide a second output representative of second data of the charged particle pencil beam; and
    a beam stop disposed at a second position distal to the second pixelated detector, the beam stop configured to provide a third output representative of an energy of the charged particle pencil beam, wherein the second pixelated detector is disposed between the isocenter plane and the beam stop;
    a diagnostics system comprising a processor and a memory, the diagnostics system configured (a) to transmit a signal to request a generation of the charged particle pencil beam at a plurality of settings; and (b) to update a calibration parameter for each setting based on at least one of the first output, the second output, and the third output.

2. The system of claim 1, wherein the settings include an energy level of the charged particle pencil beam.

3. The system of claim 2, wherein the third output is representative of a kinetic energy of the charged particle pencil beam.

4. The system of claim 2, wherein the third output is representative of a total current of the charged particle pencil beam.

5. The system of claim 1, wherein the settings include a respective trajectory of the charged particle pencil beam.

6. The system of claim 5, wherein the first data includes a first measurement of a first transverse intensity distribution of the charged particle pencil beam and the second data includes a second measurement of a second transverse intensity distribution of the charged particle pencil beam.

7. The system of claim 5, wherein the trajectory includes at least one of a deflection angle or a gantry angle.

8. The system of claim 1, wherein the settings include a respective focus of the charged particle pencil beam.

9. The system of claim 8, wherein the first data includes a first measurement of a first transverse intensity distribution of the charged particle pencil beam and the second data includes a second measurement of a second transverse intensity distribution of the charged particle pencil beam.

10. The system of claim 9, wherein the diagnostics system is configured to determine a divergence angle of the charged particle pencil beam.

11. The system of claim 1, wherein the diagnostics system is in communication with a pencil beam control system.

12. The system of claim 11, wherein the diagnostics system is configured to transmit the request signal to the control system.

13. The system of claim 11, wherein the diagnostics system is configured to transmit the updated calibration parameter to the control system.

14. The system of claim 13, wherein the control system is configured to modify a beam control signal based on the updated calibration parameter.

15. The system of claim 1, further comprising a support arm mechanically connected to the first and second pixelated detectors, the support arm mechanically connected to a motion system for adjusting a position of the first and second pixelated detectors along an axis parallel to the isocenter plane.

16. The system of claim 15, comprising a rotation mechanism mechanically connected to the first and second pixelated detectors.

17. A method for calibrating a charged particle pencil beam system, the method comprising:
    (a) transmitting a signal to request a generation of the charged particle pencil beam at a plurality of settings;
    (b) receiving, for each setting, first data representing a first transverse intensity distribution of the charged particle pencil beam at a first position, said first position proximal to an isocenter plane;
    (c) receiving, for each setting, second data representing a second transverse intensity distribution of the charged particle pencil beam at a second position, said second position distal to the isocenter plane;
    (d) receiving, for each setting, third data representing an energy measurement of the charged particle pencil beam; and
    (e) updating a calibration parameter for each setting based on at least one of the first data, the second data, and the third data.

18. The method of claim 17, wherein the settings include at least one of a focus, a magnetic field strength, a deflection angle, a gantry angle, and an energy level of the charged particle pencil beam.

19. The method of claim 17, further comprising determining a first centroid position of the first transverse intensity distribution and a second centroid position of the second transverse intensity distribution.

20. The method of claim 17, wherein updating the calibration parameter includes comparing a model beam characteristic with a measured beam characteristic.

21. The method of claim 20, wherein the model beam characteristic includes a model energy setting and the measured beam characteristic includes the energy measurement represented in the third data.

22. The method of claim 20, further comprising aligning a first pixelated detector disposed at the first position and a second pixelated detector disposed at the second position with an x-ray source.

23. The method of claim 17, further comprising adjusting at least one of the first position and the second position based on a trajectory of the charged particle pencil beam.

* * * * *